(12) United States Patent
Begg

(10) Patent No.: US 9,827,007 B2
(45) Date of Patent: Nov. 28, 2017

(54) TISSUE COLLECTION NEEDLE

(71) Applicant: Massachusetts Institute of Technology, Cambridge, MA (US)

(72) Inventor: Nikolai David Michael Begg, Wayland, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/118,743

(22) PCT Filed: Feb. 18, 2015

(86) PCT No.: PCT/US2015/016353
§ 371 (c)(1),
(2) Date: Aug. 12, 2016

(87) PCT Pub. No.: WO2015/126926
PCT Pub. Date: Aug. 27, 2015

(65) Prior Publication Data
US 2017/0042567 A1 Feb. 16, 2017

Related U.S. Application Data

(60) Provisional application No. 61/941,053, filed on Feb. 18, 2014.

(51) Int. Cl.
*A61B 5/00* (2006.01)
*A61B 17/3205* (2006.01)
(Continued)

(52) U.S. Cl.
CPC .... *A61B 17/32053* (2013.01); *A61B 10/0266* (2013.01); *A61B 17/3417* (2013.01);
(Continued)

(58) Field of Classification Search
CPC ............... A61B 10/02; A61B 10/0233; A61B 17/32053; A61B 17/3417;
(Continued)

(56) References Cited

U.S. PATENT DOCUMENTS 5,615,690 A * 4/1997 Giurtino ............ A61B 10/0266
600/567
6,517,523 B1 2/2003 Kaneko et al.
(Continued)

FOREIGN PATENT DOCUMENTS

| EP | 1297856 | 4/2003 |
| EP | 2520237 | 11/2012 |
| JP | 07100140 | 4/1995 |
| WO | WO-2015126926 | 8/2015 |

OTHER PUBLICATIONS

EPO, "International Application Serial No. PCT/US15/16353, Search Report and Written Opinion dated May 12, 2015", 11 pages.
WIPO, "PCT Application No. PCT/US15/16353 International Preliminary Report on Patentability dated Sep. 1, 2016", 9 pages.

*Primary Examiner* — Max Hindenburg
(74) *Attorney, Agent, or Firm* — Strategic Patents, P.C.

(57) ABSTRACT

A tissue collection needle with a hollow interior provides two opposing tips with beveled edges on facets that drive tissue toward the hollow interior where the tissue can be gathered and severed from surrounding tissue as the needle advances through a biological specimen. The points and bevels are advantageously formed from a minimal number of cuts amenable to rapid fabrication from readily available hollow needle stock.

11 Claims, 4 Drawing Sheets

(51) Int. Cl.
*A61B 10/02* (2006.01)
*A61B 17/34* (2006.01)
*A61M 5/32* (2006.01)
*A61B 17/00* (2006.01)
*A61B 17/32* (2006.01)

(52) U.S. Cl.
CPC . *A61M 5/3286* (2013.01); *A61B 2017/00526* (2013.01); *A61B 2017/320064* (2013.01)

(58) Field of Classification Search
CPC ......... A61B 2017/00526; A61B 2017/320064; A61M 5/32; A61M 5/3286; A61M 2037/0053
See application file for complete search history.

(56) References Cited

U.S. PATENT DOCUMENTS 9,017,299 B2* 4/2015 Iwase .................... A61M 5/158
  264/678
9,237,883 B2* 1/2016 Sundheimer ....... A61B 10/0233

* cited by examiner

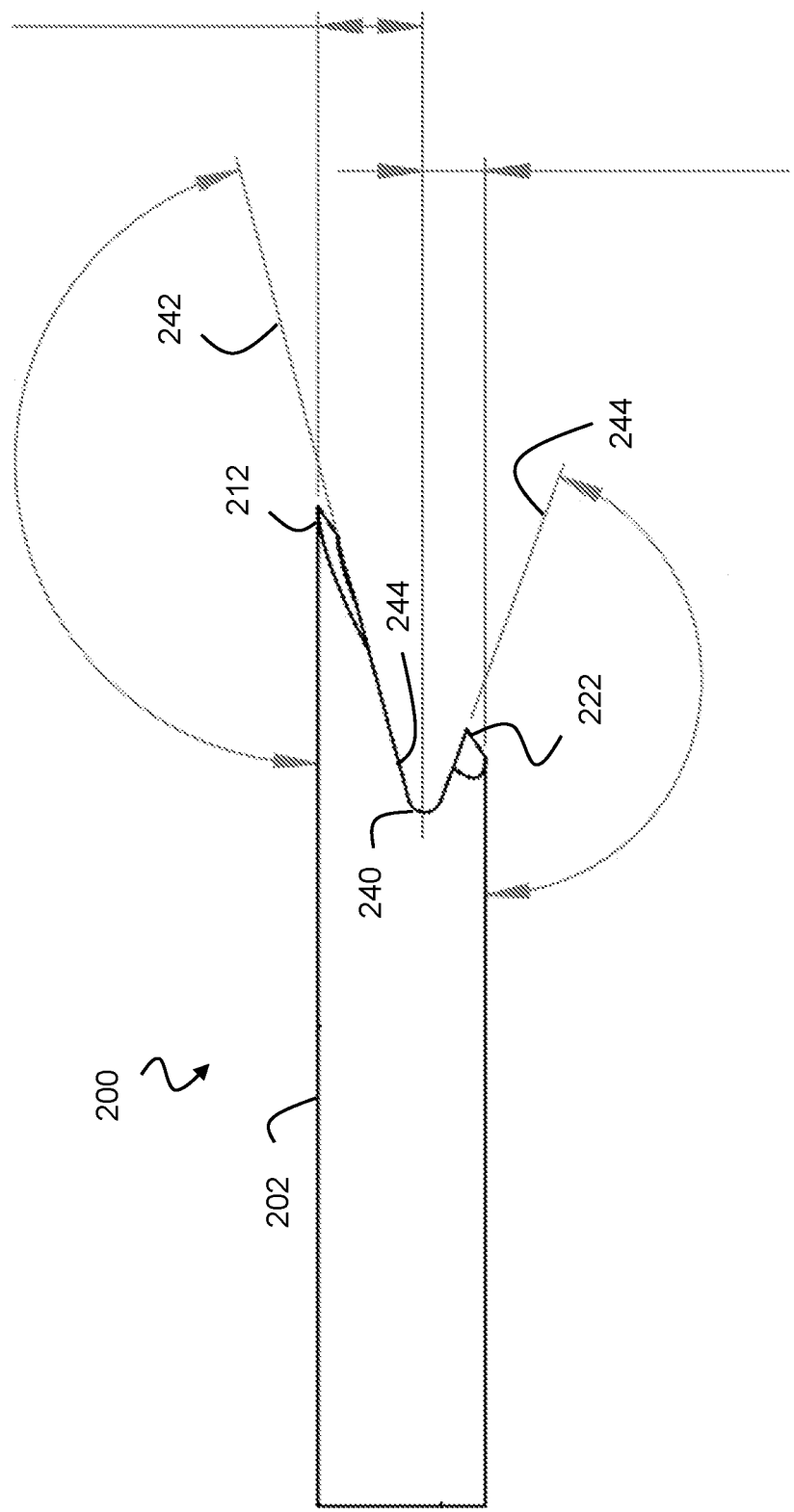

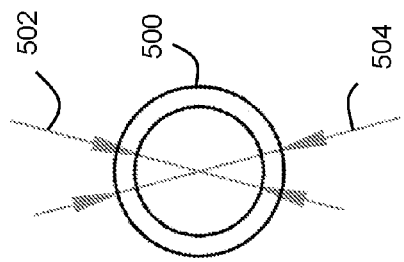
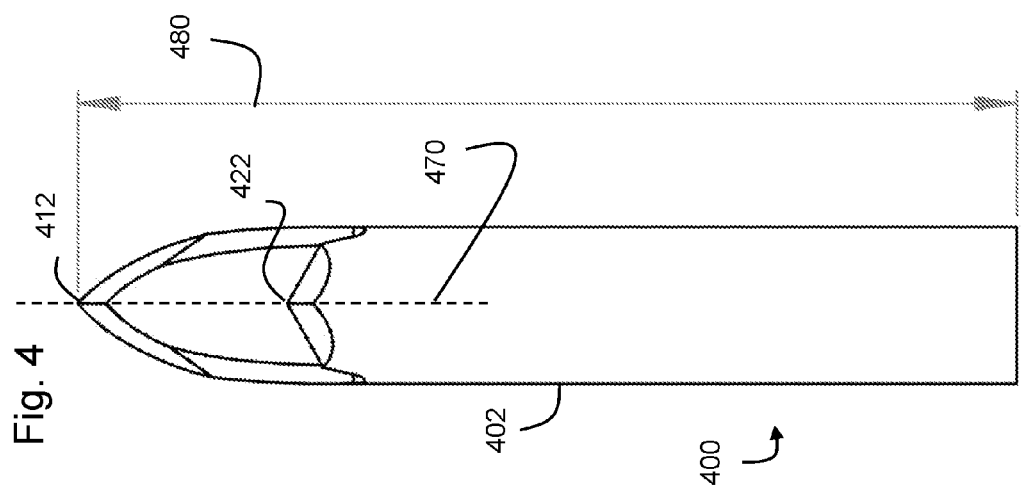
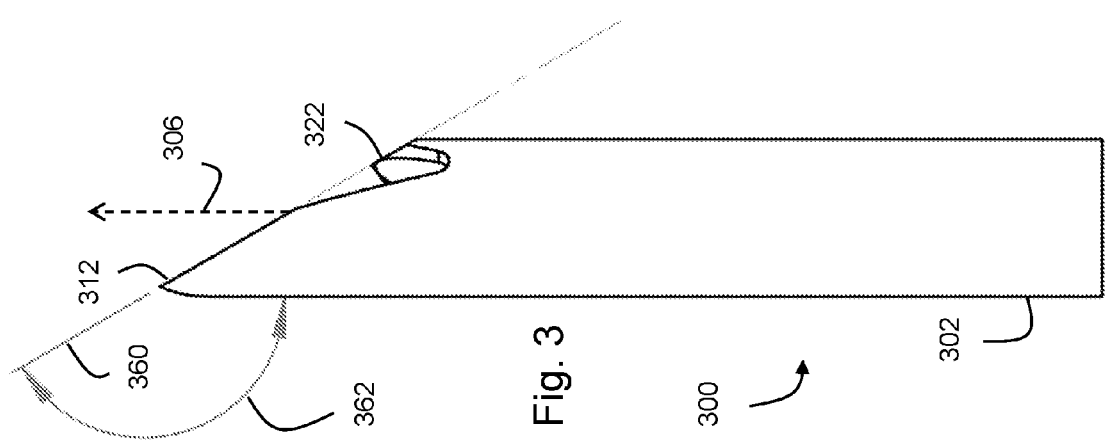

TISSUE COLLECTION NEEDLE

RELATED APPLICATIONS

This application is a national stage entry application of International Application No. PCT/US15/16353 filed on Feb. 18, 2015, which claims priority to U.S. Provisional Application No. 61/941,053 filed on Feb. 18, 2014, each of which is hereby incorporated by reference in its entirety.

BACKGROUND

There remains a need for a tissue collection needle that can be fabricated quickly and inexpensively from commonly available stock materials while providing improved tissue gather characteristics.

SUMMARY

A tissue collection needle with a hollow interior provides two opposing tips with beveled edges on facets that drive tissue toward the hollow interior where the tissue can be gathered and severed from surrounding tissue as the needle advances through a biological specimen. The points and bevels are advantageously formed from a minimal number of cuts amenable to rapid fabrication using readily available hollow needle stock.

In one aspect, a needle includes a tube having a hollow interior about an axis and an end including an opening that exposes the hollow interior, and a first tip disposed on the end, where the first tip is formed by a first pair of facets shaped to cut a biological sample and direct the biological sample toward the hollow interior from a first side of the tube. The needle may also include a second tip disposed on the end at a location on a circumference of the tube opposing the first tip, where the first tip extends further along the axis from the end of the tube than the second tip, and the second tip is formed by a second pair of facets shaped to direct the biological sample cut by the first tip toward the hollow interior from a second side of the tube opposing the first side, thereby capturing a portion of the biological sample between the first tip and the second tip as the tube advances through the biological sample and driving the portion of the biological sample into the hollow interior. The needle may further include a slot formed between the first tip and the second tip, where the slot includes a sharpened edge to cut and detach the biological sample from surrounding tissue as the biological sample enters the hollow interior of the tube.

Implementations may have one or more of the following features. A first one of the first pair of facets and a first one of the second pair of facets may lie in a first plane. A second one of the first pair of facets and a second one of the second pair of facets may lie in a second plane. The first plane may have a curvature defined by a rotary cutting tool. The second plane may have a curvature defined by the rotary cutting tool. The first plane and the second plane may be rotated about thirty degrees off the axis of the tube and about sixty degrees around the axis of the tube relative to one another. The first tip and the second tip may lie on a line where the first plane intersects the second plane. The slot may be substantially perpendicular to a line joining the first tip and the second tip. The slot may be formed by a pair of planar cuts formed diagonally into the end of the tube, where the pair of planar cuts intersects to form the slot. A first one of the planar cuts may be about fifteen degrees off the axis of the tube. A second one of the planar cuts may be about twenty degrees off the axis of the tube. The tube may have an outside diameter of about 0.050 inches and an inner diameter of about 0.038 inches. The needle may also include a stylet shaped and sized to fit within the hollow interior of the tube in sliding contact with an interior surface of the tube. The stylet may have a tip shaped to substantially coincide with a convex hull of the end of the tube including the first tip and the second tip.

In an aspect, a method for fabricating a needle includes providing a tube having an axis through a hollow interior and an open end, forming a first cut in the open end at a first angle to the axis, and forming a second cut in the open end at a second angle to the axis opposing the first angle so that the second cut meets the first cut to remove a wedge from the end of the tube, thereby providing a first tip and a second tip on opposing sides of a circumference of the tube. The method may also include forming a third cut at a third angle to the axis, where the third cut intersects the first tip and the second tip. The method may further include forming a fourth cut at a fourth angle to the axis, where the fourth cut is rotated about the axis by a rotation angle such that the third cut intersects the fourth cut in a line between the first tip and the second tip, thereby providing a cutting surface on the first tip and the second tip in the open end of the tube, with a bevel on the first tip directed toward the axis.

Implementations may have one or more of the following features. The first cut and the second cut may meet perpendicular to and offset from the axis of the tube, thereby forming an asymmetrical wedge with the first tip extending further from the open end than the second tip. At least one of the first cut, the second cut, the third cut, and the fourth cut may be formed with a rotary cutting tool. The rotary cutting tool may include a rotary blade or a rotary grinding tool. At least one of the first cut, the second cut, the third cut, and the fourth cut may be formed with an electric discharge machine cutting tool. The rotation angle between the third cut and the fourth cut may be about sixty degrees around the axis. The first cut and the second cut may meet to form a slot substantially perpendicular to the axis. The first cut may be in a plane about fifteen degrees off the axis of the tube. The second cut may be in a plane about twenty degrees off the axis of the tube. The tube may have an outside diameter of about 0.050 inches and an inner diameter of about 0.038 inches. The tube may be formed of surgical stainless steel. The method may further include providing a stylet shaped and sized to fit within the hollow interior of the tube, placing the stylet in the tube, and shaping a tip of the stylet to coincide with a convex hull of the end of the tube by forming at least the third cut and the fourth cut while the stylet protrudes through the open end.

BRIEF DESCRIPTION OF THE DRAWINGS

The foregoing and other objects, features, and advantages of the devices, systems, kits, and methods described herein will be apparent from the following description of particular embodiments thereof, as illustrated in the accompanying drawings. The drawings are not necessarily to scale, emphasis instead being placed upon illustrating the principles of the devices, systems, kits, and methods described herein.

FIG. 2 is a side view of a tissue collection needle.
FIG. 3 is a rotated rear-side view of a tissue collection needle.
FIG. 4 is a front view of a tissue collection needle.
FIG. 5 is a top view of a tissue collection needle.

DETAILED DESCRIPTION

The embodiments will now be described more fully with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," "substantially" or the like, when accompanying a numerical value or other property, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "above," "below," and the like, are words of convenience and are not to be construed as limiting terms.

Embodiments herein pertain to a novel needle tip geometry with enhanced tissue collection ability for use in biopsy and other tissue sampling procedures.

Figure 1:
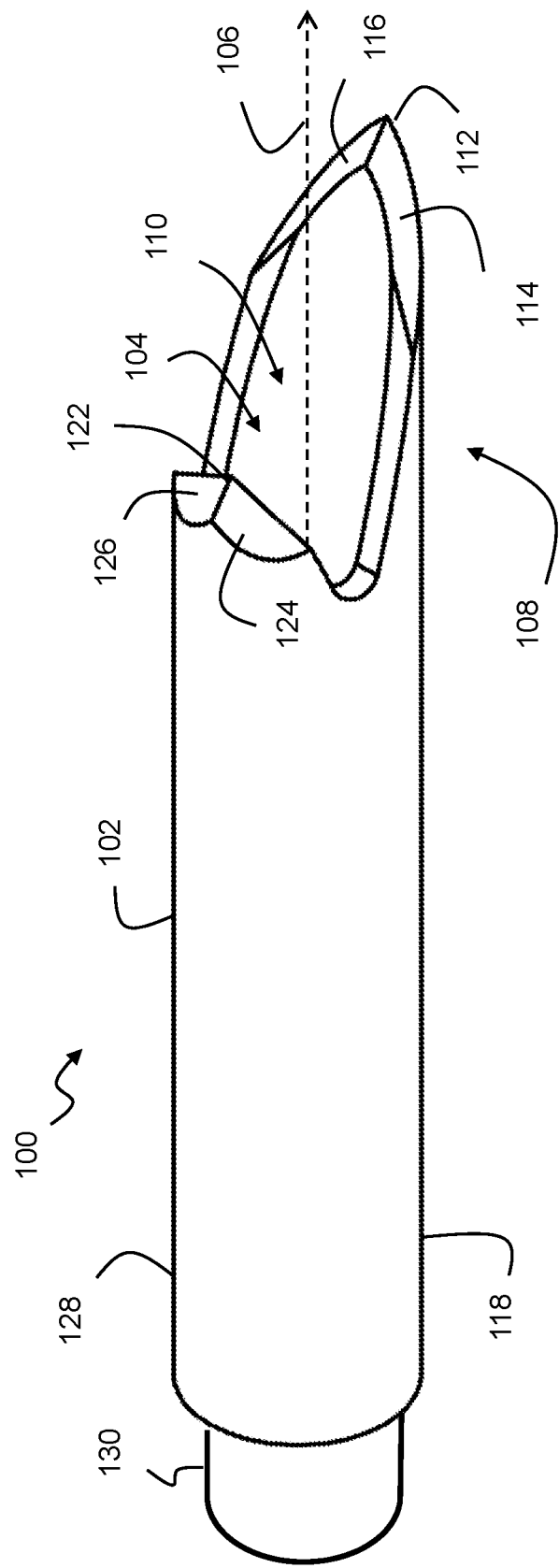
FIG. 1 is a perspective view of a tissue collection needle.

FIG. 1 is a perspective view of a tissue collection needle. In general, the needle 100 may have a tube 102 with a hollow interior 104 about an axis 106, and an end 108 including an opening 110 that exposes the hollow interior 104.

A first tip 112 may be disposed on the end 108. The first tip 112 may be formed by a first pair of facets 114, 116 shaped to cut a biological sample (not shown) and direct the biological sample toward the hollow interior from a first side 118 (generally from the bottom as depicted in FIG. 1, with tissue directed upward toward the axis 106) of the tube 102. For example, the facets 114, 116 may be planar surfaces such as flat planar surfaces or curved planar surfaces with a shape generally determined by a cutting tool used to form the planar surfaces. A line where these planar surfaces intersect may form the first tip 112 into a sharpened point. The first tip 112 may also be slightly rounded or otherwise shaped in any suitable manner for piercing tissue or the like in a biological sample as the needle 100 is driven into the biological sample. Edges of the facets 114, 116 may form sharp, cutting surfaces on the inside or outside of the tube 102 as a result of a cutting or grinding process used to form the facets 114, 116, or may be additionally sharpened or otherwise shaped or processed to improve effectiveness of the needle.

A second tip 122 may also be disposed on the end 108. The second tip 122 may be formed by a second pair of facets 124, 126 shaped to cut a biological sample (not shown) and direct the biological sample toward the hollow interior from a second side 128 of the tube 102 opposing the first side 118 (generally from the top as depicted in FIG. 1, with tissue directed downward toward the axis 106). For example, the facets 124, 126 may be planar surfaces such as flat planar surfaces or curved planar surfaces with a planar geometry generally determined by a cutting tool used to form the planar surfaces. A line where these planar surfaces intersect may form the second tip 122 into a sharpened point. The second tip 122 may also be slightly rounded or otherwise shaped in any suitable manner for piercing tissue or the like in a biological sample and gathering the tissue toward the hollow interior 104 as the needle 100 is driven into the biological sample. Edges of the facets 124, 126 may form sharp, cutting surfaces on the inside and outside of the tube 102 as a result of a cutting or grinding process used to form the facets 124, 126, or may be additionally sharpened or otherwise shaped or processed to improve effectiveness of the needle.

In general, the second tip 122 may be disposed on a circumference of the tube 102 at a location opposing the first tip 112. The first tip 112 may extend further along the axis 106 from the end 108 than the second tip 122 so that the first tip 112 leads the second tip 122 as the needle 100 is driven forward. With this configuration, the needle 100 can capture a portion of a biological specimen between the first tip 112 and the second tip 122 as the tube 102 advances through the biological sample, and drive the portion of the biological sample into the hollow interior 104. The facets 114, 116, 124, 126 may be oriented to augment this capturing function, and edges of the facets 114, 116, 124, 126 may concurrently provide a cutting edge to sever a sample gathered in this manner.

The facets 114, 116, 124, 126 may advantageously be fabricated in pairs that share planar surfaces. For example, one of the first pair of facets 114 and one of the second pair of facets 124 may lie in a first plane, such as a plane formed by a cutting tool used to fabricate the two facets 114, 124 concurrently. This first plane may have a curvature defined by a rotary cutting tool such as a rotary grinding tool. Similarly, a second one of the first pair of facets 116 and a second one of the second pair of facets 126 may lie in a second plane, such as a plane formed by a cutting tool used to fabricate the two facets 116, 126. This second plane may also have a curvature defined by a rotary cutting tool such as a rotary grinding tool, which may be the same rotary cutting tool used to form the first plane, or a different rotary tool with a different radius of curvature. In another aspect, one or more of these planes may be cut or formed using a tool that yields a flat, planar cut, such as an electronic discharge machine (EDM), a rotary saw, or band saw.

The needle 100 may optionally include a stylet 130 to aid in sample collection. The stylet 130 may be formed from a cylindrical section of raw material such as surgical stainless steel or the like shaped and sized with an outside diameter that fits within the hollow interior 104 of the tube 102 in sliding contact with an interior surface of the tube 102. The stylet 130 may be formed by placing the raw material into the tube 102 extending out of the opening 110 while making a number of planar cuts to form the first tip 112 and the second tip 122 as described above (but not extending through the opening 110 when other cuts are made to form a slot as described below). As such, the end of the stylet 130 may include two planes that, when placed in the opening 110 of the needle 100 and correctly rotationally oriented, will coincide with the two planes on the needle 100 formed by the facets 114, 116, 124, 126 of the end 108. Stated differently, the end of the stylet 130 may have a stylet tip shaped and sized to substantially coincide with a convex hull of the end 108 of the tube 102 including the first tip 112 and the second tip 122.

In general, the stylet 130 may be left inside the needle 100 when sample collection is not desired, such that the relatively continuous geometry of the stylet 130 and the end 108 of the needle 100 causes tissue or the like to be directed around the entirety of the needle 100 as the needle 100 advances. Conversely, the style 130 may be removed from the needle 100 (or at least withdrawn from the opening 110) when sample collection is desired. In this latter configuration, the first tip 112 and the second tip 122 can engage and direct a sample toward the hollow interior 104 of the needle 100 for collection.

FIG. 2 is a side view of a tissue collection needle, which may be a needle 200 such as any of the needles described above. In general, the cutting and gathering functions of the first tip 212 and the second tip 222 may be enhanced by cutting a slot 240 into the needle. The slot 240 may, for example, be formed between the first tip 212 and the second tip 222 using a pair of planar cuts including a first cut along a first plane 242 and a second cut along a second plane 244, both formed diagonally into the end of the tube 202 of the needle 200 and intersecting to form the slot 240. The planes 242, 244 may have similar or identical opposing inclines relative to the axis of the needle 200, and may intersect slightly off the axis in the center of the needle 200 to form the slot 240 substantially perpendicular to a line joining the first tip 212 and the second tip 222. For example, the slot 240 may be formed by a pair of cuts where the first plane 242 is about twenty degrees off axis and the second plane 244 is about fifteen degrees off axis in the opposing direction (i.e., rotated 180 degrees around the axis of the needle 200). It will be understood that other angles may also or instead be used, and precise symmetry around the axis of the needle 200 is not required for effective operation of the needle 200 in sample collection. It will also be appreciated that while the slot 240 may conveniently be formed after the tips 212, 224 of the needle 200, this order of fabrication steps is not strictly required, and the diagonal wedge of the slot 240 may be formed before the two planar cuts that form the sharpened tip and adjacent beveled cutting edges. The order of steps may, for example, be selected based on the order in which cutting edges are desired to be formed, the coordination with formation of a stylet of matching geometry, or any other manufacturing advantage or convenience.

The slot 240 may include a sharpened edge 244 to cut and detach a biological sample from surrounding tissue as the biological sample enters the hollow interior of the tube of the needle 200. The sharpened edge 244 may, for example, be created as an artifact of a cutting process used to form the first plane 240 and the second plane 242, or the sharpened edge 244 may be added in any suitable, subsequent sharpening process. In one aspect, the slot 200 may form a sharp corner with a radius no greater than 0.005 inches, or at a smallest radius achievable with a cutting process used to form the first plane 240 and the second plane 242.

FIG. 3 is a rotated rear-side view of a tissue collection needle such as any of the needles described above. The needle 300 may, as noted above, have a first tip 312 and a second tip 322 formed by a pair of planar cuts into an end of the needle 300. Relative to an axis 306 of the needle 300, these planar cuts 360 may have any suitable angle 362 for forming useful cutting points, such as about thirty degrees off the axis 306 of the tube 302. Each of the planar cuts 360 also has a rotational orientation about the axis, and a first plane and a second plane may be rotated about sixty degrees around the axis of the tube 302 relative to one another to form the first tip 312 and the second tip 322. This may be conveniently implemented in manufacturing by cutting, grinding, or otherwise forming a first one of the planar cuts 360 at, e.g., thirty degrees off the axis 306, and then rotating the tube 302 in a vise or other fixture about sixty degrees around the axis 306, and then repeating the planar cut 360 with the tube 302 in the new rotational orientation.

FIG. 4 is a front view of a tissue collection needle such as any of the needles described above. The pair of planar cuts used to form a first tip 412 and a second tip 422 of the needle 400 as contemplated herein may generally intersect to form a line 470 that extends across a circumference of the tube 402 and diagonally relative to the axis of the needle 400 from the first tip 412 to the second tip 422. The first tip 412 and the second tip 422 may lie on this line 470 where the two planes intersect. An overall length 480 of the needle 400 is not critical, and may depend on the intended use, e.g., the type of tissue, the location of the tissue, the amount of sample required, and so forth. In one aspect, the overall length 480 may be about 0.299 inches. Other lengths suitable for the types of human tissue that might usefully be the collected sample may be about 0.3 inches, about 0.3125 inches, or between about 0.29 inches and about 0.32 inches, or any other length. Additionally the tube 402 used to form the needle 400 may usefully be extended in a variety of circumstances such as where an extended reach of the needle 400 is desired.

FIG. 5 is atop view of a tissue collection needle such as any of the needles described herein. The needle 500 may be fashioned from any suitable material such as 18TW gauge needle stock or any other surgical stainless steel tubing or the like. In one aspect, the needle 500 may have an inside diameter 502 of about 0.038 inches and an outside diameter 504 of about 0.050 inches.

Figure 6:
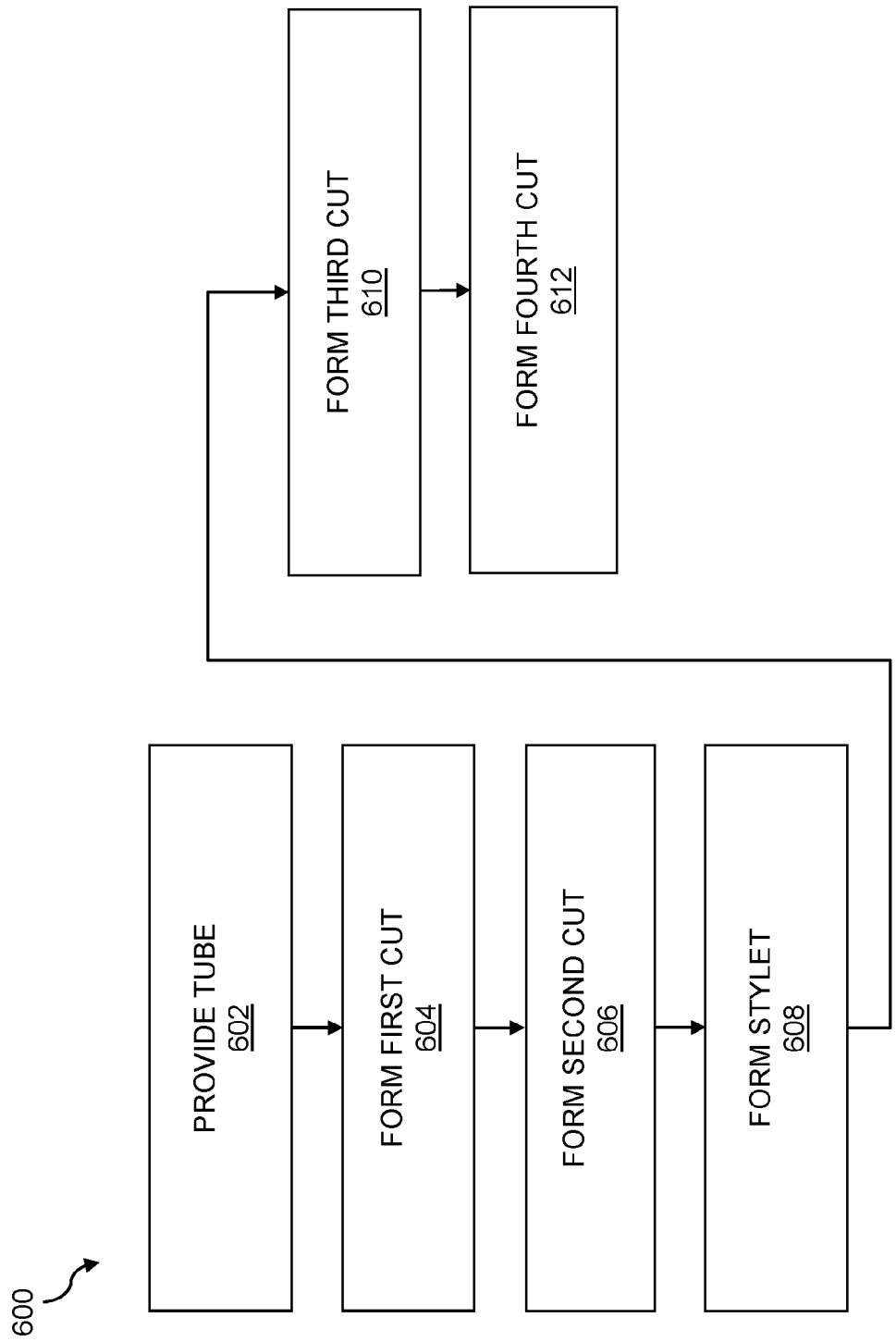
FIG. 6 shows a method for fabricating a tissue collection needle.

FIG. 6 shows a method for fabricating a tissue collection needle. In general, a method for fabricating a tissue collection needle is contemplated herein that advantageously uses a small amount of cuts to achieve a multi-pointed tissue collection needle with cutting edges beveled to drive tissue toward a tissue collection area (e.g., the center of a hollow tube) as the needle advances, along with a slot to capture and sever gathered tissue from a biological sample.

As shown in step 602, the method 600 may begin with providing a tube to fabricate the needle. The tube may be any of the tubes described above, such as 18TW gauge needle stock or any other suitably dimensioned hollow tube of surgical stainless steel or the like, and will generally have a hollow interior and an open end where the needle tips can be formed.

As shown in step 604, the method 600 may include forming a first cut in the open end at a first angle to the axis, such as about fifteen to twenty degrees off the axis of the tube. This step, and the various cutting steps described below, may be performed using any suitable cutting machinery including without limitation an electrical discharge machine (EDM) cutting tool, a rotary cutting tool (such as a rotary grinding tool or rotary blade), a band saw, or the like.

As shown in step 606, the method 600 may include forming a second cut in the open end and at second angle to the axis, such as about twenty to twenty five degrees, opposing the first angle so that the second cut meets the first cut to remove a wedge from the end of the tube, thereby providing a first tip and a second tip on opposing sides of a circumference of the tube. The first cut and the second cut may meet perpendicular to and offset from the axis of the tube to form an asymmetrical wedge with the first tip extended further from the open end of the tube than the second tip. The cuts may concurrently form a slot (at the vertex of the wedge) substantially perpendicular to the axis of the tube of the needle.

As shown in step 608, the method 600 may include forming a stylet. This may, for example, including providing a stylet shaped and sized to fit within the hollow interior of the tube, placing the stylet in the tube, and then shaping the stylet to coincide with a convex hull of the end of the tube or otherwise to match the shape of the needle. This step may advantageously be performed while the sharpened points of the needle are being formed in the steps below, e.g., by forming the cuts of steps 610-612 while the stylet protrudes through the open end of the tube. While this pair of planar cuts is made to form the two sharpened points of the needle, the end of the stylet may be concurrently formed with a matching exterior shape. Where steps 604 and 608 are performed after steps 610 and 612, the stylet may be removed in order to avoid slotting the stylet in the same manner as the needle. In another aspect, the stylet is simply shaped and sized to fit within the hollow interior of the tube, but is otherwise not shaped to coincide with a convex hull of the end of the tube or otherwise to match the shape of the end of the tube.

As shown in step 610, the method 600 may include forming a third cut at a third angle to the axis, the third cut intersecting the first tip and the second tip. The third angle to the axis may be about thirty degrees.

As shown in step 612, the method 600 may include forming a fourth cut at a fourth angle to the axis, the fourth cut rotated about the axis by a rotation angle such that the third cut intersects the fourth cut in a line between the first tip and the second tip, thereby providing a cutting surface on the first tip and the second tip in the open end of the tube, with a bevel on the first tip directed toward the axis. The fourth angle to the axis may be about thirty degrees, and/or may be equal to the third angle. The rotation angle between the third cut and the fourth cut may, for example be about sixty degrees around the axis of the tube, or between about fifty and seventy degrees, or any other rotation angle suitable for forming sharpened points and cutting surfaces as desired on the end of the needle.

While a specific order of steps is outlined below, it will be understood that the cuts contemplated herein may be performed in any useful or convenient order, provided they combine to impose the desired tip geometry contemplated herein. Thus for example, the cuts described in steps 610-612 may be made first, and then the wedge and slot may be formed with diagonal cuts into the end of the tube. Thus a manufacturing technique is described where a tissue collection needle can be fabricated using a small number of cuts into a cylindrical stock of surgical stainless steel. The position and orientation of the cuts may further reduce a need for finishing steps such as edging by placing bevels and sharpened edges at desired locations during a number of planar cutting operations used to form the needle.

It will be appreciated that the devices, systems, kits, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party, computer resource, or manufacturing device or system to perform the step of X. Similarly, performing steps X, Y and Z may include any method of directing or controlling any combination of other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method for fabricating a needle comprising:
providing a tube having an axis through a hollow interior and an open end;
forming a first cut in the open end at a first angle to the axis;
forming a second cut in the open end at a second angle to the axis opposing the first angle so that the second cut meets the first cut to remove a wedge from the end of the tube, thereby providing a first tip and a second tip on opposing sides of a circumference of the tube;

forming a third cut at a third angle to the axis, the third cut intersecting the first tip and the second tip; and forming a fourth cut at a fourth angle to the axis, the fourth cut rotated about the axis by a rotation angle such that the third cut intersects the fourth cut in a line between the first tip and the second tip, thereby providing a cutting surface on the first tip and the second tip in the open end of the tube, with a bevel on the first tip directed toward the axis, wherein the first cut and the second cut meet perpendicular to and offset from the axis of the tube, thereby forming an asymmetrical wedge with the first tip extending further from the open end than the second tip.

2. The method of claim 1 wherein at least one of the first cut, the second cut, the third cut, and the fourth cut is formed with a rotary cutting tool.

3. The method of claim 2 wherein the rotary cutting tool includes a rotary blade or a rotary grinding tool.

4. The method of claim 1 wherein at least one of the first cut, the second cut, the third cut, and the fourth cut is formed with an electric discharge machine cutting tool.

5. The method of claim 1 wherein the rotation angle between the third cut and the fourth cut is about sixty degrees around the axis.

6. The method of claim 1 wherein the first cut and the second cut meet to form a slot substantially perpendicular to the axis.

7. The method of claim 1 wherein the first cut is in a plane about fifteen degrees off the axis of the tube.

8. The method of claim 1 wherein the second cut is in a plane about twenty degrees off the axis of the tube.

9. The method of claim 1 wherein the tube has an outside diameter of about 0.050 inches and an inner diameter of about 0.038 inches.

10. The method of claim 1 wherein the tube is formed of surgical stainless steel.

11. The method of claim 1 further comprising providing a stylet shaped and sized to fit within the hollow interior of the tube, placing the stylet in the tube, and shaping a tip of the stylet to coincide with the end of the tube by forming at least the third cut and the fourth cut while the stylet protrudes through the open end.

* * * * *